United States Patent
Griffin et al.

(10) Patent No.: US 11,272,983 B2
(45) Date of Patent: Mar. 15, 2022

(54) PROCESS AND SYSTEM FOR REDUCING LASER DAMAGE TO SURGICAL INSTRUMENTS

(71) Applicant: Cyclone Biosciences LLC, Phoenix, AZ (US)

(72) Inventors: Stephen E. Griffin, Peoria, AZ (US); Jason Guth, Tempe, AZ (US)

(73) Assignee: Cyclone Biosciences, LLC, Phoenix, AZ (US)

( * ) Notice: Subject to any disclaimer, the term of this patent is extended or adjusted under 35 U.S.C. 154(b) by 199 days.

(21) Appl. No.: 15/414,706

(22) Filed: Jan. 25, 2017

(65) Prior Publication Data

US 2017/0215961 A1 Aug. 3, 2017

Related U.S. Application Data

(60) Provisional application No. 62/290,559, filed on Feb. 3, 2016.

(51) Int. Cl.
*A61B 18/20* (2006.01)
*G02B 6/42* (2006.01)
(Continued)

(52) U.S. Cl.
CPC .............. *A61B 18/20* (2013.01); *A61B 18/26* (2013.01); *G02B 6/4296* (2013.01);
(Continued)

(58) Field of Classification Search
CPC .................. A61B 18/20; A61B 18/203; A61B 2018/2035; A61B 2018/20351; A61B 2018/204; A61B 2018/2045; A61B 2018/205; A61B 2018/2055; A61B 2018/20553; A61B 18/22; A61B 2018/2205; A61B 2018/2244; A61B 2018/2247; A61B 2018/2272; A61B 2018/2277; A61B 2018/2283; A61B 2018/2288; G02B 6/42; G02B 6/4286; G02B 6/4296
USPC ..... 606/10–18, 2.5; 359/196.1, 197.1, 199.2, 359/201.2, 202.1, 223.1, 226.1, 226.2, 359/885, 888, 889, 891
See application file for complete search history.

(56) References Cited

U.S. PATENT DOCUMENTS 4,543,477 A * 9/1985 Doi .................. A61B 18/20
250/227.11
5,044,717 A * 9/1991 Levatter .............. G02B 6/4296
385/33
(Continued)

*Primary Examiner* — Ahmed M Farah
(74) *Attorney, Agent, or Firm* — Quarles & Brady, LLP; Yakov S. Sidorin

(57) ABSTRACT

Optical fibers for delivering laser energy inside the body are often tasked with traversing tortuous routes in accessing the target tissue or pathology, e.g. ureteroscopic laser lithotripsy. A common failure in such applications, known in the field as 'fiber burn through', has been known to injure patients and is a major cause of damage to ureteroscopes. Where irregular output that is produced at the start of a lasing interval passes through a fiber that is at or near the optical minimum bend limit, fail safe polymer claddings are damaged and can no longer contain even regular laser output in tight deflection. The invention disclosed provides a solution to premature fiber failure and collateral damage.

13 Claims, 6 Drawing Sheets

(51) Int. Cl.
*A61B 18/26* (2006.01)
*A61B 18/00* (2006.01)

(52) U.S. Cl.
CPC ............ *A61B 2018/00642* (2013.01); *A61B 2018/00779* (2013.01); *A61B 2018/204* (2013.01); *G02B 6/4286* (2013.01); *G02B 2006/4297* (2013.01)

(56) References Cited

U.S. PATENT DOCUMENTS

| | | | | |
|---|---|---|---|---|
| 5,154,707 A * | 10/1992 | Rink | .................. | A61B 18/22 606/12 |
| 5,387,211 A * | 2/1995 | Saadatmanesh | ....... | A61B 18/20 606/10 |
| 5,621,831 A * | 4/1997 | Staver | ................. | G02B 6/4222 250/227.2 |
| 5,729,335 A * | 3/1998 | Green | .................... | G01L 5/047 250/227.16 |
| 6,246,817 B1 * | 6/2001 | Griffin | .................. | A61B 18/22 385/43 |
| 6,539,035 B1 * | 3/2003 | Yoda | .................... | G02B 6/4206 359/619 |
| 7,090,411 B2 * | 8/2006 | Brown | ................ | G02B 6/4296 385/78 |
| 7,400,808 B2 * | 7/2008 | Seo | .................... | G02B 6/02395 385/128 |
| 2003/0216717 A1 * | 11/2003 | Nahen | .................... | A61B 18/22 606/3 |
| 2009/0149845 A1 * | 6/2009 | Brown | .................. | A61B 18/24 606/12 |
| 2009/0251697 A1 * | 10/2009 | Cutillas | ............... | H01S 5/02325 356/400 |
| 2011/0196355 A1 * | 8/2011 | Mitchell | ................ | A61B 34/25 606/11 |
| 2017/0079718 A1 * | 3/2017 | Zabar | .................... | G02B 6/4296 |

* cited by examiner

PROCESS AND SYSTEM FOR REDUCING LASER DAMAGE TO SURGICAL INSTRUMENTS

CROSS-REFERENCE TO RELATED APPLICATIONS

This disclosure claims the benefit of priority to U.S. Application 62/290,559, filed 3 Feb. 2016, the entirety of which is incorporated herein by reference.

FIELD OF THE INVENTION

A process is described for blocking errant and potentially damaging pulse energies, generated as the laser pump source(s) and/or the optical gain medium stabilize or equilibrate to operational conditions, from coupling to optical fiber energy delivery devices, reducing damage to optical fiber coatings and lowering the minimum bend radii for safe delivery of therapeutic energy. Methods of implementation of the strategy are discussed.

BACKGROUND

Lasers find utility in a variety of applications where significant pulse energies or laser powers are delivered by means of optical fibers. A limitation to delivery of laser power or energy by optical fiber is the minimum bend radius of the fiber where energy loss within the bend is sufficient to initiate catastrophic failure. This minimum optical bend radius is typically dependent upon the wavelength of the laser, the average power or peak pulse energy and repetition rate of the laser, the size and the construction of the optical fiber.

Small optical fibers are often called upon to deliver pulse laser energy to kidney stones while passing through highly deflected flexible ureteroscopes. A common failure mode of fibers within flexible ureteroscopy is popularly described as "burn through", where the fiber suddenly fractures within the scope forceps channel. Such failures are a leading cause of costly scope repairs and have even been known to injure patients by burning through the damaged scope wall.

Another failure that is similar to that described above is caused by gripping the fiber to control its position within the patient; if minimum optical bend radii are exceeded, the fiber burns through and injures the surgeon.

SUMMARY

The initial output of high power lasers is often uncharacteristically high in power or energy and/or low in $M^2$ beam quality and hot spots; light that, if coupled to an optical fiber that is at or near the optical minimum bend radius, damages the optical fiber such that subsequent, more characteristic laser emission is less competently contained than it would otherwise be had the damage been avoided. The invention described herein provides methods for avoiding fiber damage from uncharacteristic initial laser emissions, thereby enabling safer and more effective use of fiber optic laser energy delivery systems in tortuous confines such as found in ureteroscopic laser lithotripsy.

A first embodiment is a process that can include initiating, at an initiation time, a beam along a beam path from a laser source to an optical fiber; attenuating the beam reaching the optical fiber for a period of time (T1) from the initiation time; then ending the attenuation of the beam while continuing to provide the beam along the beam path.

A second embodiment is a surgical laser system that can include a laser source optically coupled to an optical fiber; a beam attenuator configured to attenuate a beam from the laser source to the optical fiber; and a controller configured to adjust a quantity of beam attenuation.

A third embodiment is a surgical laser system that can include a laser source optically coupled to an optical fiber, the laser source including a laser rod and a pump source; a beam attenuator configured to limit a transfer of energy from the pump source to the laser rod thereby attenuating a beam from the laser source to the optical fiber; and a controller configured to adjust a quantity of beam attenuation.

BRIEF DESCRIPTION OF THE FIGURES

For a more complete understanding of the disclosure, reference should be made to the following detailed description and accompanying drawing figures wherein.

While specific embodiments are illustrated in the figures, with the understanding that the disclosure is intended to be illustrative, these embodiments are not intended to limit the invention described and illustrated herein.

DETAILED DESCRIPTION

Figure 1:
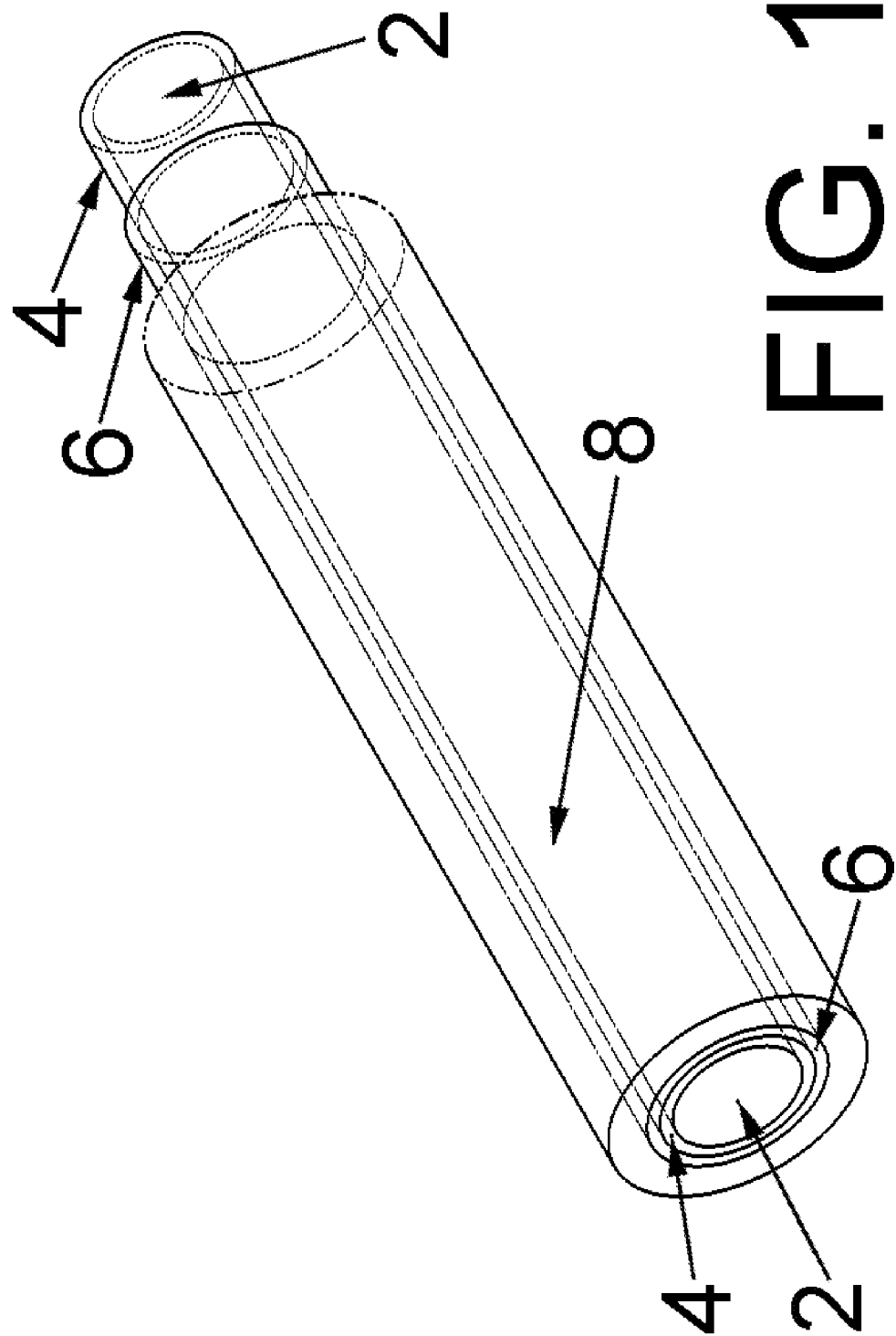
FIG. 1 is an isometric cartoon of a typical holmium laser lithotripsy fiber construction.

Optical fibers find great utility in delivering energy, for ablating and fragmenting urinary and biliary calculi, vaporizing diseased tissues, cutting and joining materials, generating plasmas for speciation of materials, among other surgical and non-surgical applications. Where the optical fiber is tasked to pass a tortuous path, for example in accessing urinary calculi located with a lower pole renal calyx, the optical minimum bend radius may be exceeded. FIG. 1 illustrates a fiber that is often used in surgical applications for containing light that would otherwise leak. The fiber core 2 is surrounded by a doped glass cladding 4 like many optical fibers. A polymer coating 6, or cladding, over the glass cladding is selected for having a lower refractive index than the glass cladding 4, and for transparency at the laser wavelength(s) of interest. A buffer layer 8 of polymer, typically ethylene tetrafluoroethylene copolymer, a polyamide or polyamide/imide copolymer, a polyaryletherketone or similar polymer, covers the polymer cladding.

Such "double clad" fibers contain light that is up converted to higher angles in tight bending (FIG. 2) by virtue of the higher numerical aperture (NA) provided by the polymer cladding 6, but polymers are not as transparent as the glass fiber for many surgical wavelengths, e.g. 2000 nm emission from thulium lasers and 2100 nm emission from holmium lasers, so some of the higher angle light that penetrates the polymer layer is absorbed and converted to heat. If too much light leaks from the glass cladding 4, the secondary cladding 6 suffers thermal damage. Damaged polymer cladding 6 is less competent for containing additional leakage, even if moderate.

Figure 2:
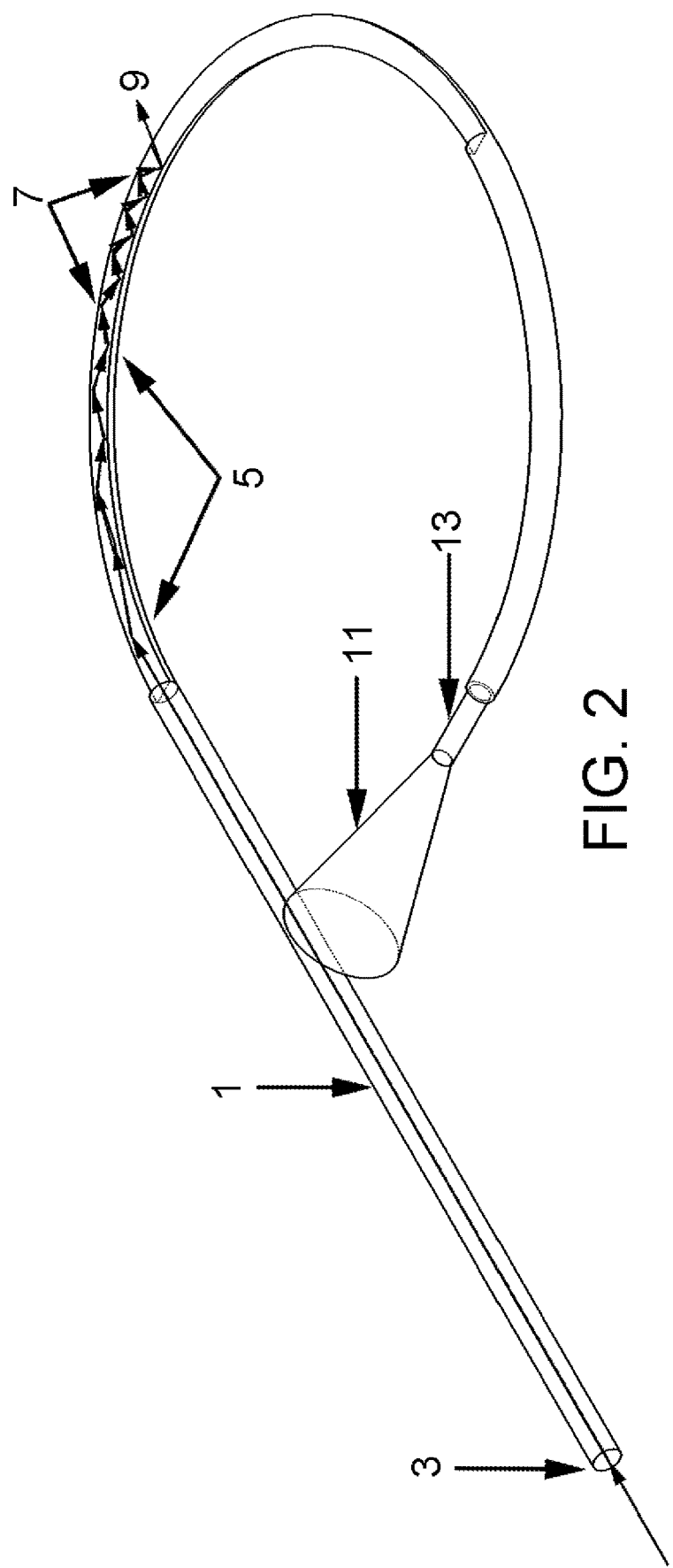
FIG. 2 is an isometric and partial section cartoon illustrating mode promotion, cladding modes and fiber leakage.

FIG. 2 illustrates up conversion beyond the secondary cladding containment in an illustration commonly employed within the art, where light is launched into the fiber 1 at the input face 3 and exits 11 at the working tip 13. Briefly, the standard model states that where the fiber 1 is bent too tightly, laser energy increases in angle of propagation within the base fiber NA ('reflects' at the core to glass cladding interface) 5 until the maximum angle for total internal reflection is exceeded and the light 'reflects' at the glass to polymer interface. Where the light continues to increase in angle of propagation 7 within the tightly curved fiber, it may exceed the maximum angle for total internal reflection for the secondary NA as well and escape 9.

Figure 3:
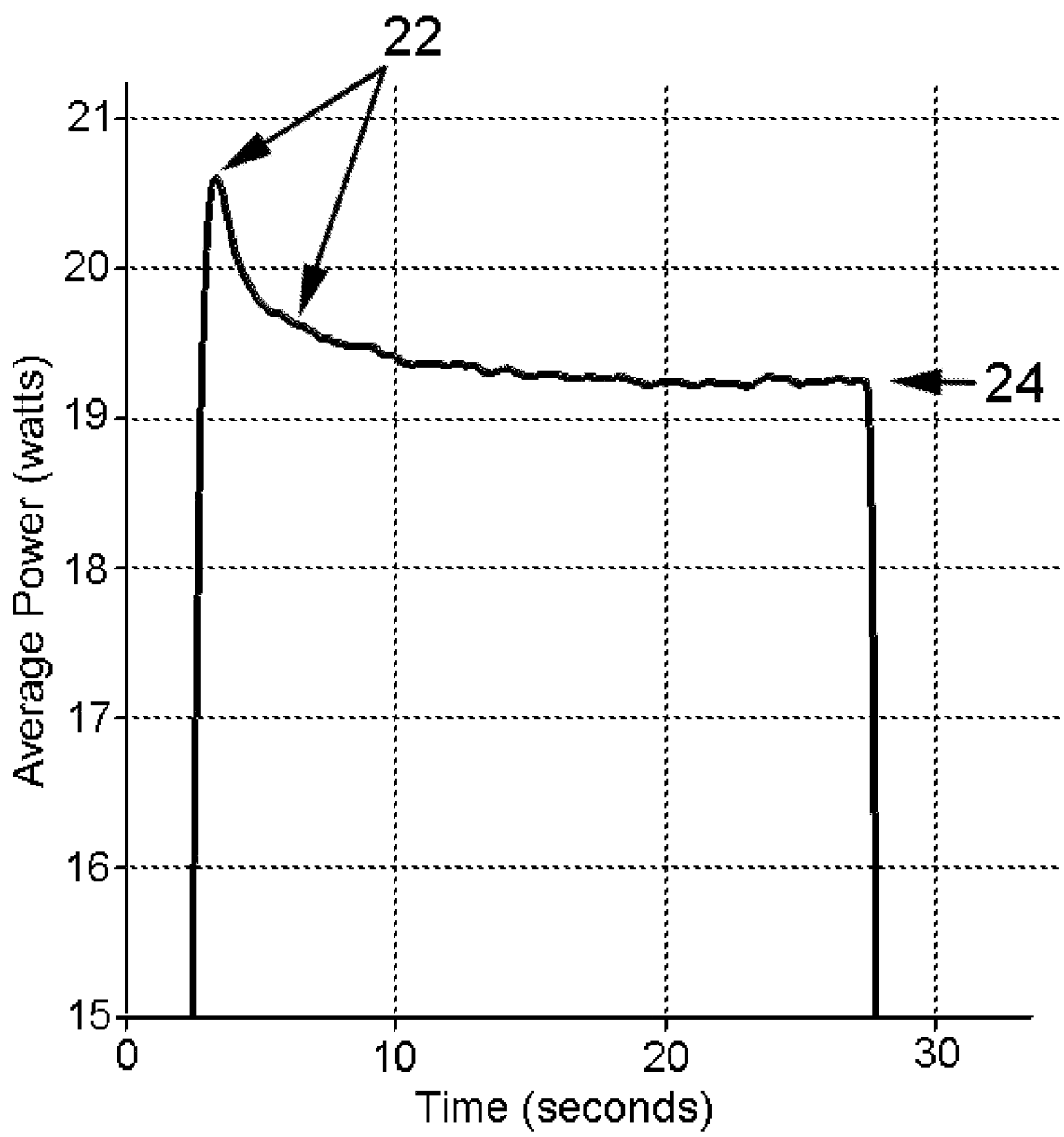
FIG. 3 is a graph of the first energy pulses produced by a typical holmium laser.

The invention described herein is based upon a more thorough treatment of the failure mechanism than provided by the standard model. Many laser sources that produce sufficient laser energy or power to affect the desired function, surgical or non-surgical, are unstable within the first half second to seconds (FIG. 3) of emission, where the laser produces significantly higher pulse energies or average power 22 and/or lower $M^2$ beam quality, including hot spots and high order modes that may be damaging to optical fiber coatings, particularly where the optical fiber is bent at, or near, the optical minimum bend radius. Normal laser output 24 traversing the damaged fiber is less effectively contained by the damaged secondary coating, leading to fiber failure at larger bend radii (or at lower power or energy) than would otherwise cause fiber failure. It should be stressed that the bend radius for causing damage varies with the fiber size and composition, the laser wavelength and the mode distribution within the fiber and that the damage caused by the early and unstable laser output occurs at larger bend radii than those where the fiber fails under normal (or stable) laser output.

This new interpretation of the failure model of fibers delivering power through tight bends is the fruit of observations made while testing holmium laser surgical fibers for safe minimum bend radii in validating new fiber optic termination designs. One test that is performed is the active bend test, where the fiber is progressively bent to tighter radii while delivering laser power. It was noted that when the initial fiber bend radius (prior to activation of the laser) is at or near the optical minimum bend radius, the fiber fails at a larger radius than where the initial bend fiber radius is larger, e.g. approximately twice the optical minimum bend radius.

A modification of the active bend test provides additional support for the new failure model. Where the laser emission is paused near to, but before the failure point average for like fibers, the fiber fails within the first few pulses when the laser is activated again. Furthermore, when the first several pulses of the laser are manually blocked with a slab of graphite, there is no difference in the bend radius at failure between fibers in active bend testing at different initial radii.

In surgical use, fibers are subjected to both active and static bending and lasing intervals are often brief and sporadic. The herein provided methods include strategies for eliminating premature failure are simple; for example, attenuate the first half second to a few seconds of laser output or prevent this errant laser output from coupling to the optical fiber altogether. In cases where the divergent output is due exclusively, or almost exclusively, to pump source instability, blocking the lasing medium from exposure to the first emissions of the pump would also be effective. Where the initial instability is characterized by greatly reduced $M^2$ beam quality in the form of high order modes, rather than simply higher energy output and hot spots, spatial filtering may be sufficient to prevent higher order modes coupling to the fiber core.

Figure 4:
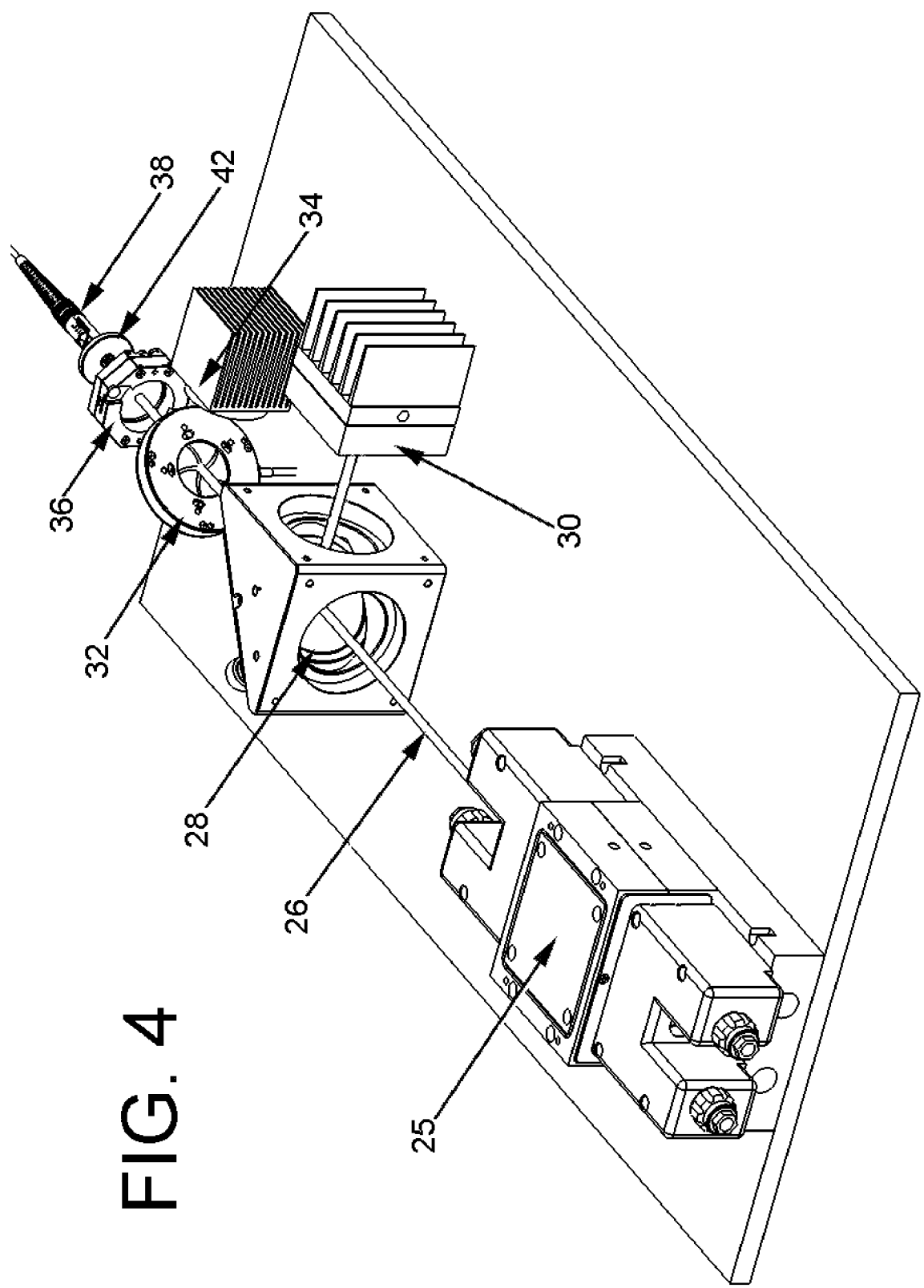
FIG. 4 is an isometric view of a typical holmium laser optical bench

FIG. 4 illustrates a typical optical layout for a holmium surgical laser where the laser head 25 (or 'brick') produces a beam 26 where the bulk of the beam 26 passes through the beam splitter 28 and a small portion of the beam 26 is reflected into a power meter 30 (alternatively called an energy meter or a monitor). A shutter 32 reflects the beam to a beam dump 34 when closed (as depicted, but with the beam passing through the shutter to define the functional beam path of interest). When the shutter 32 is opened, the beam is focused by a mounted focusing optic 36 onto an optical fiber 38 aperture housed within a fiber connector and installed within the laser port 42.

Figure 5:
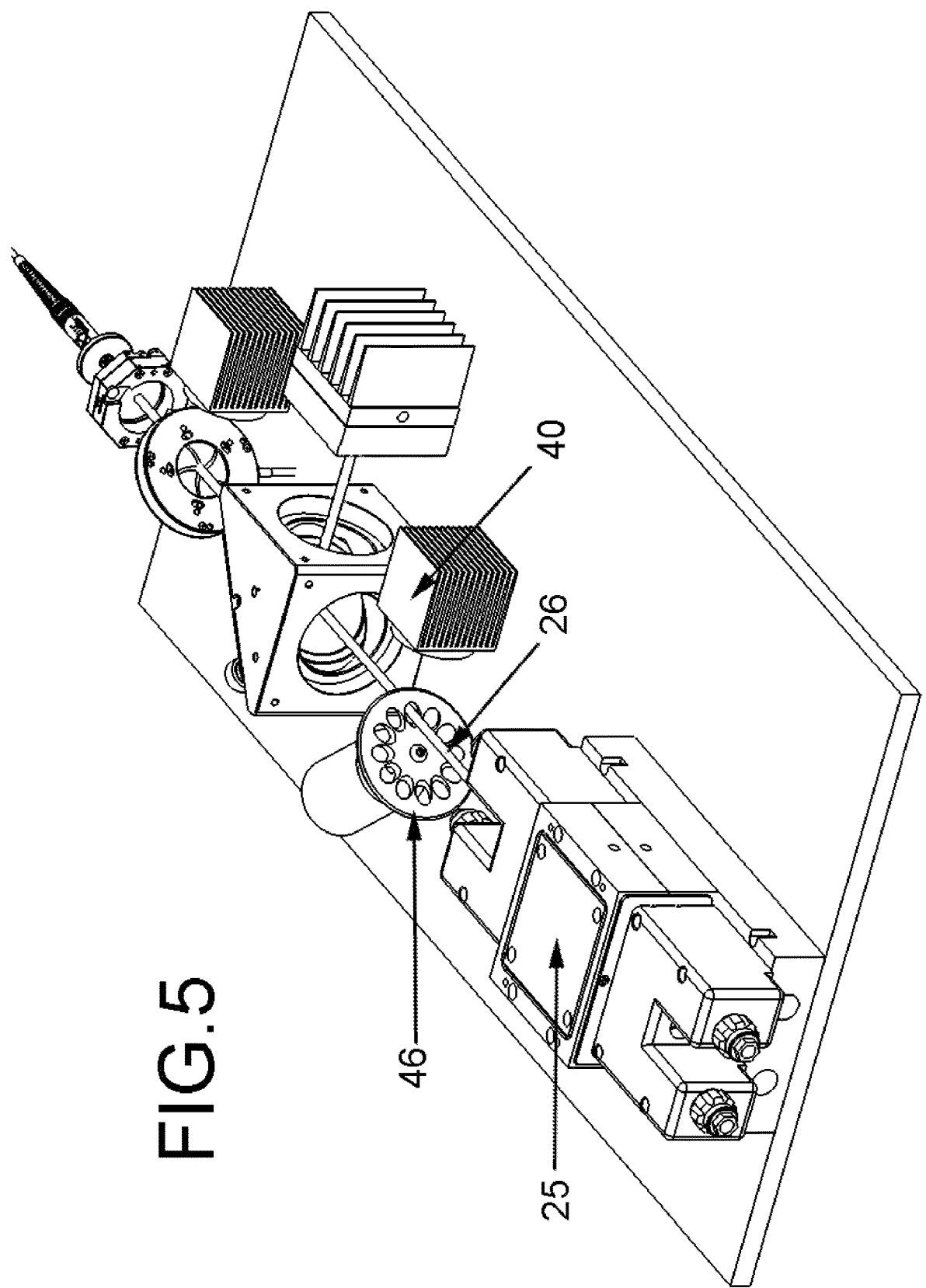
FIG. 5 is an isometric view of a typical holmium laser with the preferred embodiment installed.

FIG. 5 is identical to FIG. 4 with the addition of the preferred embodiment: a chopper blade 46 with a plurality of 45 degree and oversized (relative to the laser beam) holes that is rotated to attenuate the beam by partially reflecting some of the beam 26 into a beam dump 40 (or beam sink) while permitting the bulk of the beam 26 to pass. When the chopper blade 46 is stopped it does so in a reproducible rotational position such as to not attenuate the beam. The chopper blade need not have this specific construction in order to function and, in fact, may be equipped with a spatially filtering hole for passing the beam in the stopped position, or a larger hole at the stopped position to insure no spatial filtering occurs, depending upon laser output stability characteristics.

Alternatively, attenuation or blocking the laser output may be accomplished at the laser pump. Reflectors may be arranged to temporarily block or attenuate pump emission from stimulating laser emission within the gain medium, or the pump elements may be actuated at something less than full emission for the initiation of laser emission. Other embodiments of workable solutions include a mirror to completely divert the beam during the period of unstable laser output, a beam splitter to temporarily attenuate the beam, a stationary spatial filter that is reflective or absorptive, a movable neutral density filter, and a movable chopper blade.

Simply delaying the opening of the shutter by a software change is likely to yield undesirable results for surgical lasers where shutters are typically included as a failsafe against uncontrolled emission, mandated by regulatory authorities, rather than as a means for active modulation of the laser beam. Software changes to gently raise the laser emission at initiation maybe effective in specific laser designs where $M^2$ beam quality is not a major component of the damaging early emission and if the energy rise is gradual enough, but delaying the delivery of full surgical effect may also have undesirable consequences. In addition, time need not be the variable for determining when it is appropriate to remove diversion or attenuation from the beam path: the laser power may be monitored before a diverting element and before or after an attenuation mechanism to determine when it is safe to allow the full laser output to pass to the fiber aperture.

Therefore, in a first embodiment, the herein disclosed system can include a laser source coupled to an optical fiber; a beam attenuator configured to attenuate a beam from the laser source to the optical fiber; and a controller configured to adjust a quantity of beam attenuation. Preferably, the system is a surgical laser system; for example, an endoscopic laser surgical system comprising, at a minimum, a laser, an optical fiber and an endoscope.

In one instance, the laser source can be a holmium laser. In another instance, the fiber includes a bend with a bend radius at about an optical minimum bend radius; preferably, the optical minimum bend radius for a system utilizing a holmium laser. In yet another instance, the controller can be configured to reduce beam attenuation after about 0.1 to about 20 seconds.

The beam attenuator is, preferably, positioned along a beam path from the laser source to the optical fiber. The beam attenuator can include a beam sink, for example a beam sink trap with a heat sink. In one preferable instance, the controller is configured to remove the beam attenuator from the beam path.

Figure 6:
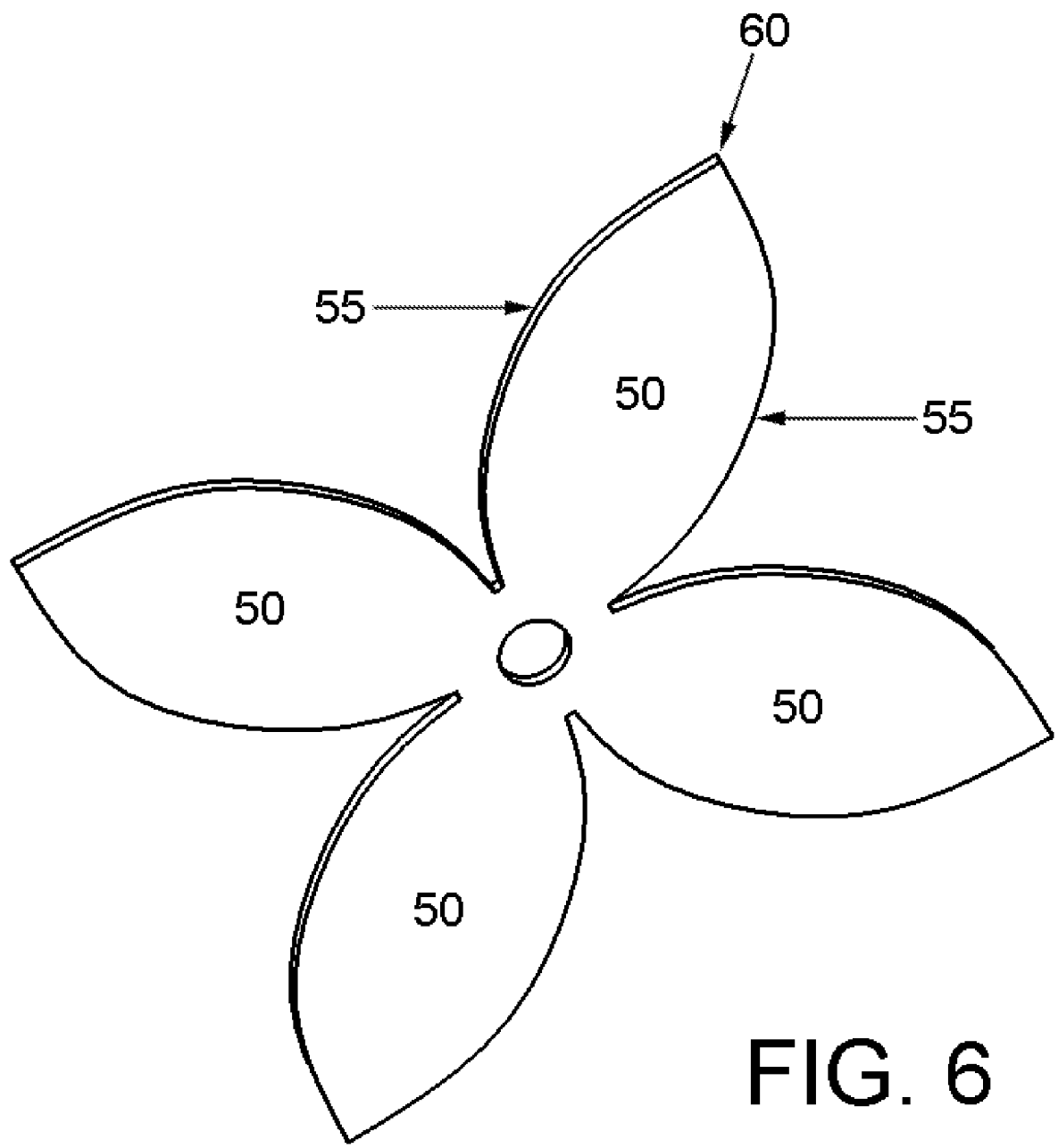
FIG. 6 is an isometric view of a specialized optical chopper blade.

The beam attenuator includes (or can be) a beam splitter; preferably wherein the beam splitter is positioned at an angle of about 45° relative to the beam path. The beam splitter can be a stationary reflector or an optical chopper. In one instance, the beam splitter includes an optical chopper positioned at an angle of between about 10° to about 80°, about 20° to about 70°, or about 30° to about 60° relative to the beam path. That is, the rotational axis of a chopper wheel is about 10°, 20°, 30°, 40°, 45°, 50°, 60°, 70°, or 80° off of the beam path. In another preferable instance, the beam sink is configured to capture light reflected from the optical chopper. In another instance, illustrated in FIG. 6, the optical chopper includes a chopper wheel that includes vanes 50 having non-radial edges 55. That is, the edges of the reflective vanes of the chopper wheel are not radial edges (not linearly extending from a center point) but preferably converge at the outside edge of the chopper wheel 60. In one instance, the reflective vanes 50 have curved edges 55 that converge at the outside edge 60 of the chopper wheel. In still another instance, the optical chopper can be a tuning fork optical chopper. Preferably, the percentage of the beam blocked by the optical chopper can be adjusted by the controller.

The system can further include a monitor that is configured to measure output from the laser source. The monitor can measure the beam power, the beam profile, coherency, or combinations of these beam characteristics. Preferably, the monitor provides an output identifying the beam characteristics. In one instance, the controller is configured to reduce beam attenuation pursuant to this output from the monitor. In another instance, the controller is configured to remove the beam attenuator from the beam path when the output from the laser source is within 10%, 5%, or 1% of an output standard.

In another embodiment, the system can include a laser source optically coupled to an optical fiber, the laser source including a laser rod and a pump source; a beam attenuator configured to limit a transfer of energy from the pump source to the laser rod thereby attenuating a beam from the laser source to the optical fiber; and a controller configured to adjust a quantity of beam attenuation. Preferably, the system is a surgical laser system; for example, an endoscopic laser surgical system. In one instance, the laser system includes a monitor configured to measure output from the laser source. Additionally, the laser system can include a controller that is configured to reduce limitation on the transfer of energy from the pump source to the laser rod.

Yet another embodiment is a process that can include providing or initiating a beam along a beam path from a laser source to an optical fiber; attenuating the beam reaching the optical fiber for a period of time (T1), the T1 beginning when the beam is initiated; then ending the attenuation of the beam while continuing to provide the beam along the beam path. In one preferred instance, the optical fiber is a surgical fiber, for example a flexible endoscope-compatible optical fiber. While the period of time during which the beam is attenuated (T1-period) can vary, the T1-period is preferably less than 50%, 40%, 30%, 20%, or 10% of the total time beam time. In one instance, the T1-period is about 0.01 to about 20 seconds; about 0.25 to about 10 seconds; or about 0.5 to about 5 seconds. In yet another instance, the beam quality (e.g., power, profile, and coherence) is monitored and the T1-period is determined based on a variation of the beam quality from an output standard. For example, the beam quality can be monitored at a location along the beam path prior to the optical fiber. Preferably, the T1-period terminated when the beam quality (e.g., beam power) reduces to within 25%, 20%, 15%, 10%, or 5% of the output standard. Preferably, the beam output standard is understood to mean the average power, profile and coherence for the beam based on the input power and stability of the lasing elements, for example, an output standard based on the average output power can be observed in FIG. 3 at between 20 and 26 seconds from the initiation of the beam.

While the process is applicable to many different laser systems, the process, preferably, includes an optical fiber that has a bend having a bend radius at about an optical minimum bend radius. Furthermore, the process, preferably, includes a laser source that is a holmium laser.

The attenuation of the beam can be accomplished by a variety of methods, disclosed herein; in one instance, attenuating the beam can include providing a beam attenuator in the beam path. In this instance, ending the attenuation can include removing the beam attenuator from the beam path. Preferably, the beam attenuator (during the T1-period) diverts less than 50%, 40%, 30%, 20%, or 10% of the beam from reaching the optical fiber. In one instance, the beam attenuator includes a beam splitter positioned to divert a portion of the beam to a beam sink.

The beam attenuator can be or can include a stationary spatial reflector and/or a rotating or vibrating optical chopper. In one instance the stationary spatial reflector and/or the optical chopper is positioned at an angle of between about 10° to about 80°, about 20° to about 70°, about 30° to about 60°, or about 40° to about 50° relative to the beam path. That is, the rotational axis of a chopper wheel or the face of the stationary spatial reflector can be about 10°, 20°, 30°, 40°, 45°, 50°, 60°, 70°, or 80° off of the beam path.

In one instance, the beam attenuator includes a stationary spatial reflector that can be a v-groove reflector and/or a comb reflector. Notably, the term stationary spatial reflector does not convey that the position of the reflector cannot move (i.e. the process includes the removal of the reflector from the beam path to end attenuation) but that this reflector is not in motion while affecting the attenuation of the beam. By contrast, the beam attenuator can be an optical chopper that rotates at a high frequency or a tuning fork chopper that moves a reflective plate into the beam at a set (or variable) frequency.

In another instance, the beam attenuator includes an optical chopper that has a chopper wheel. In one instance, the chopper wheel includes vanes having non-radial edges. In still another instance, the optical chopper can be a tuning fork optical chopper.

In yet another example, attenuating the beam can include attenuating the laser pump. For example, attenuating the laser pump can be affected by reducing an amount of light reaching the laser rod from the pump source. In one instance, the pump source can be at least one diode (e.g., laser diode or pump diode). Here, attenuating the laser pump can include reducing the number of diodes pumping the laser rod and/or reducing (e.g., blocking) a percentage of light from the pump source from reaching the laser rod.

In another instance, the pump source can be one or more flash lamps. Notably, attenuating the laser pump can includes reducing the number of flash lamps pumping the laser rod and/or reducing the amount of light reaching the laser rod from the flash lamps.

What is claimed:

1. A process for preventing a damage of a bent optical fiber configured for transmission of a laser output therethrough, the process comprising:
    switching on a laser source to generate the laser output of a chosen duration directed towards and aligned with said optical fiber;
    attenuating said laser output starting at a moment of the switching for a period of time to prevent an errant portion of the laser output from being coupled into said optical fiber; and
    reducing a degree of said attenuating after said period of time to couple an un-attenuated laser output into said optical fiber.

2. The process of claim 1,
    wherein said switching on the laser source includes switching on the laser source to generate a pulsed laser output that is aligned with said optical fiber.

3. The process of claim 1, wherein the period of time is within a range from 0.01 second to 20 seconds.

4. The process of claim 1, wherein said switching includes switching a holmium laser or a thulium laser to generate a pulsed laser output at a wavelength suitable for surgical applications.

5. The process of claim 1, further comprising monitoring a power of said laser output at a location along the beam path and prior to the optical fiber.

6. The process of claim 5,
    wherein said laser output is a pulsed laser output, and
    wherein said reducing includes reducing the degree of attenuation when an average power of said pulsed laser output reaches a value within 10% of an average power of said pulsed laser output.

7. The process of claim 1, wherein the attenuating includes diverting less than 50% of the laser output from being coupled in said optical fiber with the use of a beam attenuator placed in an optical path of the laser output.

8. The process of claim 7, wherein the attenuating includes chopping said laser output with an optical chopper having a vane dimensioned to not linearly extend from a center of the optical chopper.

9. The process of claim 7,
    wherein the attenuating includes chopping said laser output with an optical chopper having a vane dimension to have a first width at a first radial distance from a center of the optical chopper, a second width at a second radial distance from the center of the optical chopper, and a third width at a third radial distance from the center of the optical chopper,
    wherein the second width is larger than the first width and the second width is larger than the third width.

10. The process of claim 1, wherein said attenuating includes attenuating said laser output with an optical chopper positioned in an optical path of said laser output at 10° to 80° relative to the path.

11. The process of claim 1, comprising coupling said laser output into the optical fiber configured for use in an ureteroscopic laser lithotripsy.

12. A process for preventing a damage of a bent optical fiber configured for transmission of a laser output therethrough, the process comprising:
    switching on a laser source to generate the laser output of a chosen duration directed towards said bent optical fiber;
    attenuating said laser output with an optical chopper, which is positioned in an optical path of said laser output at 10° to 80° to said optical path, starting at a moment of the switching for a period of time to prevent an errant portion of the laser output from being coupled into said optical fiber; and
    reducing a degree of said attenuating after said period of time to couple an un-attenuated laser output into said optical fiber.

13. The process according to claim 12, wherein the attenuating includes chopping said laser output with the optical chopper having a vane dimensioned to not linearly extend from a center of the optical chopper.

* * * * *